United States Patent [19]

Schwartz

[11] 4,421,505
[45] Dec. 20, 1983

[54] WOUND IRRIGATION SYSTEM

[76] Inventor: Nathan H. Schwartz, 2205 Haverhill Ct., Marietta, Ga. 30067

[21] Appl. No.: 380,108

[22] Filed: May 20, 1982

Related U.S. Application Data

[63] Continuation-in-part of Ser. No. 345,003, Feb. 2, 1982.

[51] Int. Cl.³ .............................................. A61M 1/00
[52] U.S. Cl. ........................................ 604/28; 604/290
[58] Field of Search .................... 604/27, 28, 35, 51, 604/289, 290, 313, 315, 118, 119

[56] References Cited

U.S. PATENT DOCUMENTS

| | | | |
|---|---|---|---|
| 946,256 | 1/1910 | McNerthney | 604/35 |
| 1,114,268 | 10/1914 | Kells | 604/27 |
| 1,758,332 | 5/1930 | Pittman et al. | 604/35 |
| 2,568,566 | 9/1951 | Sokolik | 604/35 |
| 3,993,080 | 11/1976 | Loseff | 604/28 |
| 4,098,275 | 7/1978 | Consalvo | 604/27 |

Primary Examiner—John D. Yasko
Attorney, Agent, or Firm—B. J. Powell

[57] ABSTRACT

A method of irrigating a wound in a body part with a treatment liquid including the steps of placing a piece of tubing having a perforated section therein in the body part so that the perforated section is located in the vicinity of the wound in the body part to be irrigated; connecting one end of the tubing to a source of the treatment liquid so that the treatment liquid passes through the tubing into the body part and is discharged into the wound through the perforated section; and connecting the opposite end of the piece of tubing to a vacuum source so that a vacuum can be imposed through the tubing on the treatment liquid passing into the body part through the tubing and through the perforated section on any liquid in the body part to withdraw same. The apparatus for carrying out the method is also disclosed.

9 Claims, 14 Drawing Figures

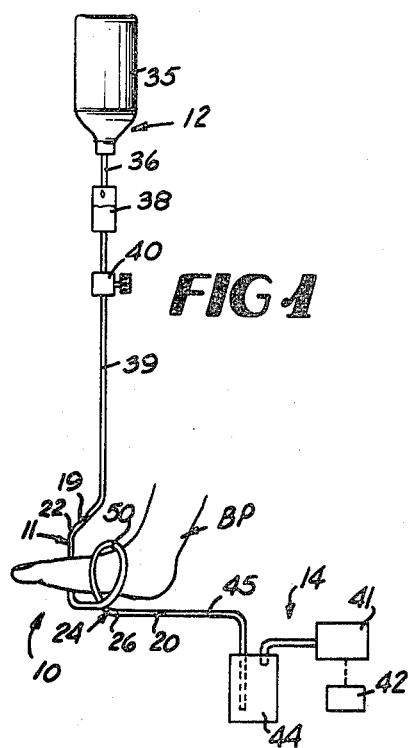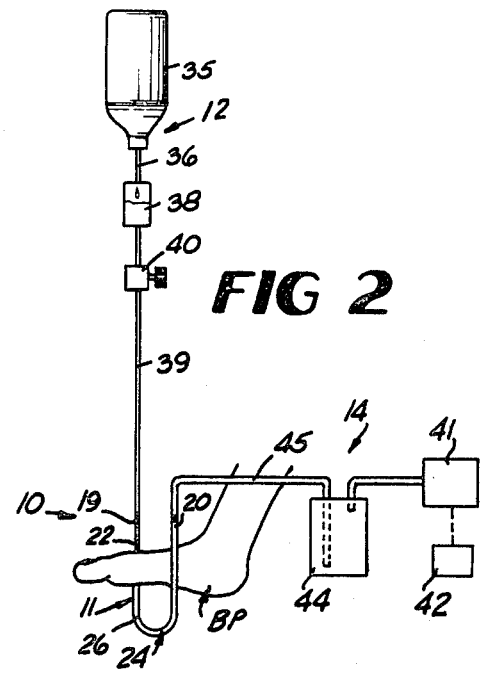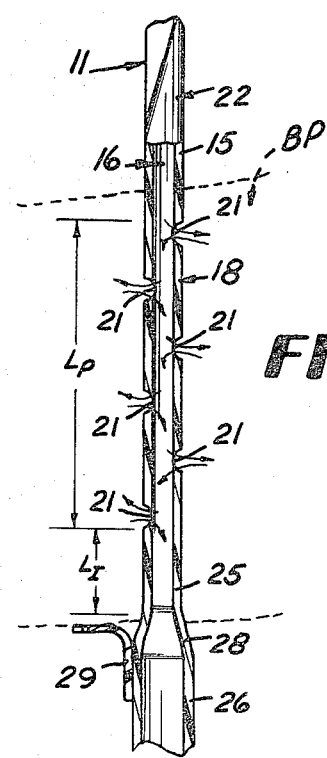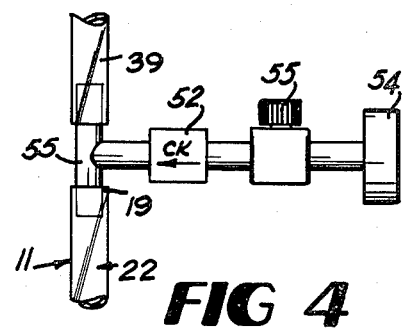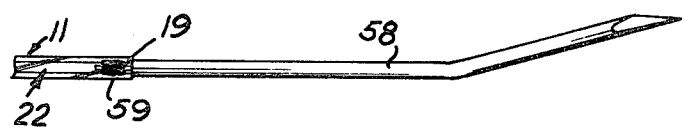
FIG 1
FIG 2
FIG 3
FIG 4
FIG 5

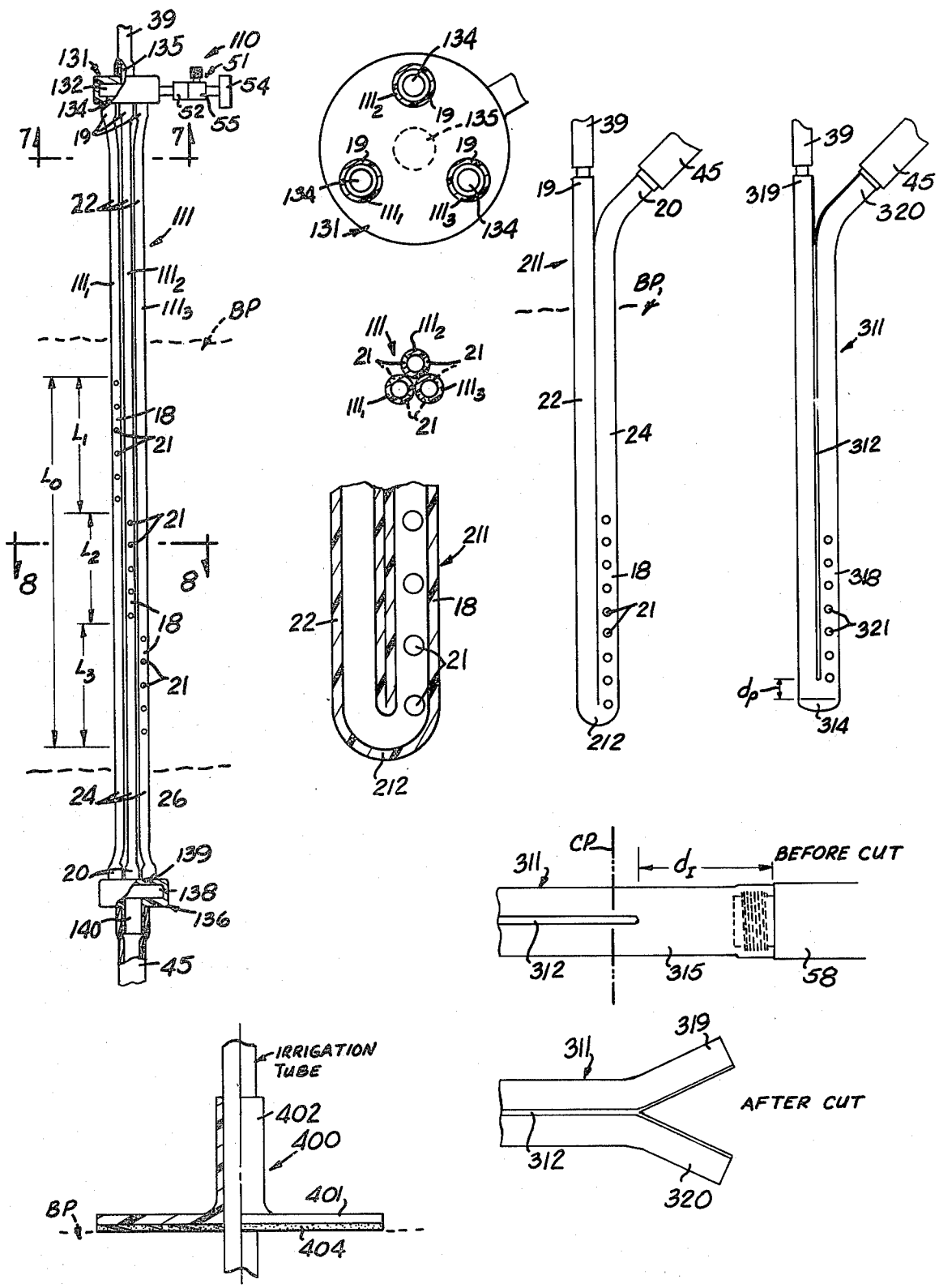

WOUND IRRIGATION SYSTEM

CROSS REFERENCE TO RELATED APPLICATION

This application is a continuation-in-part of my copending application Ser. No. 345,003, filed on Feb. 2, 1982.

BACKGROUND OF THE INVENTION

This invention relates generally to irrigation apparatus and more particularly to irrigation apparatus for use in irrigating portions of body parts with a treatment solution to prevent or reduce infection.

Irrigation of a portion of a body part with a treatment solution quite often becomes necessary to prevent or reduce infection. Where the body part has a natural cavity therein, such as a bladder or other similar organ, catheterization has been used to introduce the treatment solution into the organ and to drain fluid from the organ by gravity. Where the body part has no such natural cavity as is the case with bones, muscles and the like or a foot, arm, hand or the like, the treatment solution is typically introduced into the body part through a perforated section in a piece of tubing. Another piece of tubing connected to a vacuum source is positioned in the body part at a position spaced from the injection tubing so that the treatment solution must migrate through the body part from the injection tubing to the vacuum tubing before being withdrawn. Both of these prior art irrigation techniques have problems associated with the use thereof. One of the primary problems associated therewith is that the drain from the body part frequently becomes blocked, thereby requiring frequent monitoring to see if the drain is blocked. Further appropriate cleaning techniques must be used to clear this blockage. Another problem associated therewith is that surgical procedures are frequently required to install and/or remove the irrigation apparatus from the body part.

SUMMARY OF THE INVENTION

These and other problems associated with the prior art are overcome by the invention disclosed herein by providing an irrigation apparatus and technique which is not subject to drain blockage and which can be installed without resort to surgical procedures.

The irrigation apparatus of the invention includes a piece of tubing that is passed through the body part. The tubing has a fluid passage therethrough and is provided with a perforated section corresponding in length to that portion of the body part to be irrigated. The perforated section is located in registration with that portion of the body part to be irrigated. One end of the tubing is connected to a fluid source for supplying the treatment solution to the fluid passage in the tubing at a controlled rate while the other end of the tubing is connected to a vacuum source.

The fluid source continuously supplies treatment solution to the fluid passage in the tubing while the vacuum may be intermittently imposed in the fluid passage in the tubing. Thus, while the vacuum is not being imposed, the treatment solution flows along the fluid passage and is forced out through the perforated section of the tubing into the body part. When the vacuum source is operating, a vacuum is imposed through the perforated section of the tubing to withdraw the fluid in the body part around the perforated section of the tubing out of the other end of the tubing. At the same time, however, the vacuum is also imposed on the treatment fluid between the fluid source and the perforated section in the tubing so that some of this treatment fluid is also withdrawn through the other end of the tubing along with the fluid from the body part to keep the fluid passage in the tubing flushed out. Since fluid is alternately discharged out through the perforated section and then sucked in through the perforated section, this action keeps the perforations open to prevent blockage of the perforations.

Since the tubing passes through the body part, installation is simplified. A solid needle is fitted in one end of the piece of tubing and passed through the body part pulling the tubing therebehind. After the tubing is in place, the needle is removed and the connections made to carry out the irrigation procedure.

A venting means is provided between the fluid source and body part to permit air to be drawn through the tubing in the body part when a vacuum is being imposed. This permits a sufficient volume to be withdrawn to insure that the fluid from the body part will be withdrawn when the vacuum is imposed.

To insure that the treatment fluid will flow through all of the perforations in the irrigation tube, the length of the perforated section in the tube should be limited to a prescribed short length. In order to provide for an irrigation length in the body part greater than this prescribed short length, several pieces of tubing may be used together with the perforated section in each piece of tubing longitudinally offset from the perforated sections in the other pieces of tubing so that each short length perforation in each tubing will irrigate a portion of the total irrigation length in the body part. All of the pieces of tubing are connected to a common fluid source and to a common vacuum source so that the pieces of tubing are in parallel with each other.

Further, to reduce contamination when the irrigation tubing is removed from the body part, the irrigation tube may be formed in a loop with the sides of the loop lying against each other so that the irrigation tubing passes into and out of the body part through a common opening. This allows the irrigation tubing to be removed from the body part without cutting the pieces of and thus prevent contamination of the body part. The perforated section in the piece of tubing is located on the egress side of the loop from the body part to insure that the irrigation fluid will be supplied to the body part for irrigation.

Further, to prevent the irrigation tubing from flexing at the point where it enters the body part so as to irritate and inflame the body part in this area, a mounting adapter is provided. The mounting adapter may be mounted at the ingress, egress, or both sides of the body part and is provided with an upstanding tubular section that holds the flexible irrigation tubing passing therethrough in a fixed position with respect to the tubular section. One end of the tubular section is provided with an enlarged base section which is fixedly attached to the outside of the body part. The enlarged base section distributes any side forces that may be exerted on the surface of the body part over a large area so that the body part will not be irritated at the point of entry or exit of the irrigation tubing, and the point at which the irrigation tubing flexes is shifted from the surface of the body part out to the projecting end of the tubular section on the mounting adapter.

These and other features and advantages of the invention disclosed herein will become more apparent upon consideration of the following specification and accompanying drawings wherein like characters of reference designate corresponding parts throughout the several views and in which:

BRIEF DESCRIPTION OF THE DRAWINGS

FIG. 1 is a view illustrating the invention;

FIG. 2 is a view similar to FIG. 1 illustrating a different arrangement of the invention, FIG. 3 is an enlarged longitudinal cross-sectional view of a portion of the irrigation tube of the invention;

FIG. 4 is an enlarged view showing a venting means for the invention;

FIG. 5 is a view illustrating an installation needle for use with the invention; and FIG. 6 is a side elevational view illustrating another embodiment of the invention using multiple irrigation tubes;

FIG. 7 is an enlarged cross-sectional view taken generally along line 7—7 in FIG. 6;

FIG. 8 is an enlarged cross-sectional view taken generally along line 8—8 in FIG. 6;

FIG. 9 is a side elevational view illustrating another embodiment of the invention incorporating a looped irrigation tube;

FIG. 10 is an enlarged portion of FIG. 9 showing the looped end of the irrigation tube and a portion of the perforated section therein;

FIG. 11 is a side elevational view illustrating another version of the looped irrigation tube;

FIG. 12 is an enlarged view of a portion of that embodiment of the invention shown in FIG. 11 illustrated prior to being installed in the body part;

FIG. 13 is a view similar to FIG. 12 with the irrigation tube cut after installation for connection to the fluid and vacuum sources; and FIG. 14 is an enlarged view shown partly in cross-section of a mounting adapter used to mount the irrigation tubing in the body part.

These figures and the following detailed description disclose specific embodiments of the invention; however, it is to be understood that the inventive concept is not limited thereto since it can be incorporated in other forms.

DETAILED DESCRIPTION OF ILLUSTRATIVE EMBODIMENTS

Referring to the drawings, the irrigation system 10 includes an elongate irrigation tube 11 adapted to be passed through the body part BP to be irrigated, a fluid source 12 connected to one end of the irrigation tube 11, and a vacuum source 14 connected to the opposite end of the tube 11. The treatment solution is supplied from the fluid source 12 to the body part via tube 11 and fluids are withdrawn from the body part by the vacuum source 14 via the tube 11. While the system 10 is illustrated being applied to a foot, it is to be understood that the system 10 may be easily used to irrigate any body part or portion thereof such as a hand, leg, arm, finger, toe or the like.

The irrigation tube 11 has a seamless tubular side wall 15 defining a fluid passage 16 therethrough along the length of tube 11. Side wall 15 is typically made out of a flexible plastic material. Side wall 15 has a perforated section 18 therein intermediate its ends with a prescribed length $L_P$ adapted to be located in the portion of the body part BP to be irrigated. The tube 11 is installed in the body part BP so that the perforated section 18 is in registration with that portion to be irrigated and with opposite ends 19 and 20 of the tube 11 projecting out of the body part. That end 19 of tube 11 is adapted to be connected to the fluid source 12 while that end 20 of tube 11 is adapted to be connected to vacuum source 14.

The perforated section 18 of side wall 15 defines a plurality of discharge openings 21 therethrough axially spaced along section 18 and circumferentially spaced about section 18. These openings 21 communicate with the fluid passage 16 so that fluid can flow from passage 16 out through openings 21 or into passage 16 through openings 21 as will become more apparent. The diameter of openings 21 is smaller than the diameter of fluid passage 16 to help prevent blockage of passage 16 as will become more apparent.

For purposes of identification, that section of tube 11 between the perforated section 18 and end 19 will be called the inlet section 22 while that section of the tube 11 between the perforated section 18 and end 20 will be called the discharge section 24. Typically, the inlet section 22 has the same diameter as the perforated section 18 and this section is passed through the body part to locate the perforated section 18 in registration with that portion of the body part BP to be irrigated as will become more apparent. The discharge section 24 may likewise have the same diameter as the perforated section 18, although, in the arrangement illustrated in FIGS. 1–5, the discharge section 21 has an inboard portion 25 of the same diameter as the perforated section 18 with a length $L_I$ such that the portion 25 extends from the perforated section 18 to the exterior of the body part BP. Section 21 also has an outboard portion 26 connected to the inboard portion 25 by a tapered transition portion 28. The outboard portion 26 has a larger diameter than the perforated section 18 with the transition portion 28 tapering inwardly from the diameter of portion 26 down to the diameter of inboard portion 25. The transition portion 28 also serves to provide a seal around the tube 11 at the surface of the body part BP as will become more apparent. An attachment tab 29 may be provided on the discharge section 24 at the transition portion 28 for attaching the tube 11 to the body part BP such as by suturing to hold the tube 11 in place during use.

It will be appreciated that the tube 11 will be made in different sizes so that the diameter of the fluid passage 16 through the perforated section 18 will be of different sizes. This is necessary to provide for the different flow rates of the treatment fluid to be used to irrigate the body part BP and to insure that the perforated section 18 is small enough to be placed in different body parts BP. It will also be appreciated that the tube 11 will be made with perforated sections 18 of different lengths $L_P$ so that a tube 11 can be selected with a perforated section 18 therein that matches the length of that portion of the body part BP to be irrigated. Likewise, where the discharge section 24 has an inboard portion 5 and an outboard portion 26, different sizes of tubes 11 will be provided where the length $L_I$ of the inboard portion will be different to accommodate different sizes of body parts BP. In each instance, it will be appreciated that each of the discharge openings 21 has a diameter smaller than the diameter of the fluid passage 16 through the perforated section 18 so as to prevent material from entering the fluid passage 16 through the discharge openings 21 which have a size sufficiently large to block the fluid passage 16.

With respect to the length $L_P$, it has been found that the length $L_P$ must be selected so that fluid will pass out through and/or pass in through the discharge openings 21 in the perforated section 18 along the entire length $L_P$. If a length $L_P$ too long is selected, then the discharge openings 21 at the center of the perforated section 18 will not have fluid passing out of the passage 16 into the body part BP from the fluid source 12 nor will fluid from the body part BP be drawn into the fluid passage 16 through these central discharge openings. The length $L_P$ to insure that fluid is either passing out through discharge openings 21 and/or in through the discharge openings 21 along the entire length of the perforated section is dependent on a number of factors including the diameter of the fluid passage 16, the size of the discharge openings 21 and the number of these discharge openings along the length of the perforated section 18 as well as the pressure of the fluid supplied to the perforated section 18 from the fluid source 12 and the amount of vacuum imposed in the fluid passage 16 from the vacuum source 14. It has been empirically found that the length $L_P$ of the perforated section 18 should be no greater than three inches under typical hospital operational conditions and preferably should be less than two inches to insure that there is fluid movement through all of the discharge openings 21 along the length of the perforated section 18.

The irrigation tube 11 may be installed in the body part BP during a surgical procedure or may be installed without resorting to a surgical procedure. When the irrigation tube 11 is to be installed without a surgical procedure, a solid needle 58 commonly known in the medical profession as a trocar seen in FIG. 5 may be used. Such trocars are conventionally available and are equipped with a threaded portion 59 on one end thereof designed to be screwed into the end of a piece of tubing to pull the tubing through the body part. The threaded portion 59 is selected so as to be screwed into the end 19 of the inlet section 22 of the tube 11. Preferably, the outside diameter of the trocar 58 should be equal to or slightly greater than the outside diameter of the inlet section 22 of the tube 11. The trocar 58 can then be inserted through the body part and pulled to pull the tube 11 into place in the body part with the inlet section 22 passing therethrough followed by the perforated section 18. The tube 11 is pulled through the body part until the perforated section 18 is located in registration with that portion of the body part to be irrigated. This usually causes the transition portion 28 in the discharge section 24 to engage the surface of the body part to seal tube 11 thereto. It will be appreciated that the body part may be internally viewed through a fluoroscope as the trocar 58 is inserted therethrough. Likewise, the tube 11 may be trated with an appropriate material so that the tube 11 may be seen with the fluoroscope as it is installed in the body part so that the perforated section 18 can be accurately located within the body part. After the tube 11 is installed in the body part BP, the trocar 58 is removed and the fluid source 12 and vacuum source 14 are connected thereto to complete the system.

Various fluid sources 12 may be used in the invention. The particular fluid source 12 illustrated is an I.V. bottle 35 typically supported at an elevated position on an appropriate stand (not shown) so that its height above the patient can be adjusted. The bottle 35 is filled with the desired treatment solution to be used and its outlet tube 36 is connected to a conventional drop chamber 38. The outlet of drop chamber 38 is in turn connected to the end 19 of the inlet section 22 of irrigation tube 11 by a piece of tubing 39 equipped with a flow control valve 10 so that the treatment fluid flows by gravity into tube 11.

The rate of flow of the treatment fluid out of the bottle 35 is controlled by valve 40 and can be visually monitored in drop chamber 38. While valve 10 is illustrated as a manually adjustable valve, automatic flow regulating mechanisms as are known in the art may be substituted therefor. The treatment fluid thus flows down the fluid passage 16 in irrigation tube 11 toward the perforated section 18 at the rate established by the valve 10. It will also be appreciated that the treatment fluid is flowing into tube 11 continuously. While the flow rate may be varied as required, it has been found that flow rates of one drop/5 sec. to one drop/sec. are adequate for most applications.

Various vacuum sources 14 may be used with the invention. The particular vacuum source 14 illustrated is a vacuum pump 41 equipped with a controller 42 to control the operation of pump 41. The inlet to vacuum pump 41 is connected to the discharge of a vacuum receiver 44 while the inlet to the vacuum receiver 44 is connected to the end 20 of the discharge section 24 of the irrigation tube 11 by a piece of tubing 45. It will thus be seen that, when the vacuum pump 11 is operating, a vacuum will be imposed in the fluid passage 16 through the irrigation tube 11 via the vacuum receiver 41 and the tube 45. The controller 42 is constructed and arranged to intermittently operate the vacuum pump 41 so as to intermittently impose a vacuum in the fluid passage 16 in tube 11. The controller 12 may be adjustable so that the duration of the "on" cycle and the "off" cycle of the vacuum pump 41 may be adjust able. The time that the vacuum is not being imposed should be adjusted to permit adequate diffusion of the treatment fluid into the body part.

One vacuum pump which has been used satisfactorily has a built-in controller and is sold commercially by Gomco Surgical Manufacturing Corp. of Brooklyn, New York, as their Model 76A Thermontic Drainage Pump. This particular pump has a fixed cycle of 15-20 seconds "on" followed by 4-8 seconds "off" and can be used to supply vacuums of 120 mm mercury or 90 mm mercury. Typically, the higher vacuum is used. The vacuum pump 41 may be continuously operated and still obtain irrigation of the wound or may be intermittently operated as mentioned above. During intermittent operation, the treatment fluid from the fluid source 12 will flow down the fluid passage 16 in inlet section 22 of the irrigation tube 11 and will be discharged therefrom out through the discharge openings 21 of the perforated section 18 of the tube 11 into the body part BP around the tube 11 when the vacuum pump 41 is not operating. This allows the treatment fluid to diffuse into the body part. It will also be appreciated that the treatment fluid will continue to diffuse into the body part as well as being withdrawn therefrom while the vacuum pump is operating.

When the vacuum pump is operating, however, it will be seen that the vacuum imposed in the fluid passage 16 through tube 11 will draw treatment fluid along the passage 16 through the perforated section 18 and the discharge section 21 of the tube 11. Also, the vacuum is imposed through at least some of the discharge openings 21 in the perforated section 18 of the tube 11 on the fluids surrounding the perforated sections of the tube 11 in the body part BP. This causes the fluids in the body part BP to be withdrawn therefrom through the openings 21 into the fluid passage 16 and then withdrawn out through the discharge section 24 in the tube 11. The treatment fluid in the inlet section 22 withdrawn through the discharge section 21 without flowing out through the openings 21 keeps the fluid passage 16 in the perforated section 18 and discharge section 24 clear. During intermittent operation, the time that the vacuum is being imposed should be selected to prevent an excessive amount of the treatment fluid in the inlet section 22 of the tube 11 from being withdrawn during the "on" cycle. During continuous vacuum operation, the amount of vacuum is selected to prevent an excessive amount of treatment fluid in the inlet section 22 of the tube 11 from being withdrawn without being diffused into the body part.

As soon as the vacuum pump 41 ceases its operation, the vacuum is removed and the treatment fluid continues flowing down the inlet section 22 passing out into the body part BP through the openings 21. This alternating flow out through the discharge opening 21 into the body part BP and from the body part BP into the tube 11 through the openings 21 keeps the openings 21 cleared of any blockage due to any free floating material in the body part BP such as blood clots. This alternate discharge of the treatment fluid through the openings 21 into the body part and the subsequent withdrawal of the treatment fluid together with any fluids that become intermixed therewith in the body part BP serves to keep the body part BP flushed to reduce the likelihood of infection.

Although the intermittent operation of the vacuum source 14 is preferred, it will be appreciated that some of the treatment fluid will diffuse into the body part BP through openings 21 even though the vacuum source 14 is continuously operating. This is because some of the treatment fluid will pass out into the body part through those openings 21 nearer the inlet section 22 of tube 11 and then be withdrawn back into the tube 11 through the openings 21 nearer the discharge section 24.

The treatment fluid may be any of a variety of fluids such as a sterile saline solution or such a solution with any appropriate medication mixed therein. Thus, the irrigation system is to be used to keep the body part clean and/or to treat the body part with appropriate medication to reduce any infection.

It will be appreciated that some retention means should be provided for maintaining back pressure in the perforated section 18 of the tube 11 to assist in the treatment fluid flowing into the perforated section 18 through the inlet section 22 and out through the discharge openings 21 into the body part BP. Such a retention means serves to restrict the treatment fluid from simply flowing along the fluid passage 16 into the discharge section 24 without significantly flowing out through the openings 21. To provide this retention means, FIG. 1 shows a loop 50 formed in the discharge section 21 after it passes out of the body part BP. By using loop 50, the vacuum pump 41 is free to withdraw the fluid through the discharge section 24; however, the treatment fluid flowing from the fluid source 12 when the vacuum is not operating will fill the loop 50 up to a level sufficiently to cause the treatment fluid to be forced out of the discharge openings 21 into the body part BP. Typically, the uppermost portion of the loop 50 is at least as high as the uppermost discharge openings 21 through the perforated section 18 and preferably is located at a level about equal to that where the tube 11 enters the body part BP. The loop 50 should be located as close as practical to the point where tube 11 exits the body part to minimize the volume of fluid required to force the treatment fluid out through opening 21.

FIG. 2 shows an alternate method of providing a back pressure to force the treatment fluid out through the discharge openings 21 in the tube 11 when the vacuum pump 41 is not operating. This procedure provides locating at least the vacuum receiver 44 above the level of the body part BP so that the discharge section 24 of the tube 11 extends upwardly above the level of the perforated section 18 in the tube 11. Thus, the treatment fluid from the source 12 will flow along the discharge section 24 of the tube 11 until the treatment fluid is forced out of the discharge openings 21 of the perforated section 18. In both of these instances, it will be seen that the tube 11 is located in the body part BP so that the inlet section 22 passes into the body part BP through the top of the body part BP while the discharge section 24 exits the body part BP through its bottom. It will be appreciated that the direction in which the tube 11 extends through the body part BP may be used to provide the back pressure necessary to force the treatment fluid out of the openings 21 through the perforated section 18 when the vacuum pump 41 is not operating.

It has further been found that it is sometimes difficult to impose a sufficient vacuum in the fluid passage 16 through the tube 11 to insure that the fluid will be withdrawn from the body part BP together with a sufficient amount of the treatment fluid entering the tube 11 to keep the tube 11 clean. This is especially true where the size of the fluid passage 16 through the tube 11 is very small. To assist in the withdrawal operation, a venting means 51 may be provided between the body part BP and the fluid source 11 as illustrated in FIG. 4, so that, when a vacuum is imposed in the fluid passage 16 through the tube 11, air can be drawn into the fluid passage 16 and passed therethrough along with any fluid in passage 16 while the vacuum pump 11 is operated. The venting means 51 includes a check valve 52 operating so as to only allow air to enter the passage 16 through the tube 11. The check valve 52 may be provided with an appropriate filter 54 to keep the air passing into the fluid passage 16 clean. To regulate the amount of air passing into tube 11, a regulating valve 55 may be provided. While the venting means 51 may be connected to the system at any position between the body part BP and the fluid source 12, it is preferable that the venting means 51 be located as close as possible to the body part BP. One convenient location is to locate the venting means 51 on the connector 56 connecting the end of the inlet section 22 to the tubing from the fluid source 12. Likewise, it will be appreciated that additional fluid may be injected into the tube 11 through the venting means 51 under sufficient pressure to clear any unusual blockage that may occur in the fluid passage 16 and/or discharge openings 21 in the tube 11.

FIGS. 6-8 illustrate another embodiment of the invention where it is desirable to irrigate a length of the body part greater than the length $L_P$ of the perforated section 18 in the irrigation tube 11. The system is designated generally by the reference numeral 110 with only the irrigation tube assembly 111 being illustrated which is connected to the fluid source 12 and the vacuum source 11 in a manner similar to that described with the first embodiment of the invention.

As best seen in FIG. 6, the injection tube assembly 111 includes a plurality of irrigation tubes $111_1$–$111_3$ which are connected in parallel to the fluid source 12 and the vacuum source 11. While three such irrigation tubes are illustrated, it will be understood that any reasonable number of irrigation tubes can be used depending on the length of that portion of the body part to be irrigated.

In the irrigation assembly 111 illustrated, each of the irrigation tubes $111_1$–$111_3$ has a side wall 15 defining the fluid passage 16 therethrough similarly to the first embodiment of the invention while the perforated section 18 in each which defines the discharge openings 21 therethrough similar to that of the first embodiment of the invention. The perforated section 18 in the irrigation tube $111_1$ has a length $L_1$ while that of the irrigation tube $111_2$ has a length $L_2$ and that of the irrigation tube $111_3$ has a length $L_3$. It will further be appreciated that the perforated sections 18 in the irrigation tubes $111_1$–$111_3$ are actually displaced with each other so that the discharge openings 21 in the perforated sections 18 sum to give an accumulative overall irrigation length $L_0$ which is equal to the sum of the lengths $L_1$–$L_3$.

The irrigation tubes $111_1$–$111_3$ may be installed as a unit in the body part or may be individually installed in generally a side-by-side fashion in a manner such as that described for the first embodiment. It will further be appreciated that irrigation tubes $111_1$–$111_3$ can be arranged in different configurations within the body part to change the area that is being irrigated to any desired configuration.

It is important that all of the tubes $111_1$–$111_3$ be connected to the common fluid source 12 and common vacuum source 14 for sake of economy and simplicity of operation. To do this, an inlet connector 131 is provided as seen in FIGS. 6 and 7 which defines a transfer chamber 132 which is provided with three outputs 134 to be connected to the inlet ends 19 of the irrigation tubes $111_1$–$111_3$. The chamber 132 is also provided with an inlet 135 which is connected to the tubing 39 which serves as the outlet from the fluid source 12 in a manner similar to that illustrated with the first embodiment of the invention. It will thus be seen that the inlets 19 to the irrigation tubes $111_1$–$111_3$ are connected in parallel so that the fluid passing out of the tubing 39 will be divided in the connector 131 between the irrigation tubes $111_1$–$111_3$.

Likewise, an outlet connector 136 is provided to be connected to the exit ends 20 of the irrigation tubes $111_1$–$111_3$. The outlet connector 136 defines a transfer chamber 138 therein which is provided with three inputs 139 to be connected to the exit ends 20 of the irrigation tubes $111_1$–$111_3$. The chamber 138 is also provided with an outlet 110 which is connected to the tubing 45 which serves as an inlet to the vacuum source 14.

The irrigation assembly 111 operates similarly to the first embodiment of the invention. The incoming treatment fluid from the fluid source 12 is divided between the tubes $111_1$–$111_3$. The fluid withdrawn from the body part BP into the tubes $111_1$–$111_3$ is combined before it reaches the vacuum receiver 44.

When the irrigation tubes 11 or $111_1$–$111_3$ are used, it will be seen that these tubes pass into the body part at one position and pass out of the body part at another position. When these tubes are removed, it is necessary that one end of the tube originally outside of the body part be pulled through the body part as the tube is removed. This causes undesirable contamination of the body part.

FIGS. 9 and 10 illustrate another embodiment of the irrigation tube which overcomes this problem. The irrigation tube in this embodiment has been designated by the reference numeral 211. As best seen in FIG. 9, the irrigation tube 211 has a 180° bend 212 formed in the inlet section 22 thereof just upstream of the perforated section 18. The perforated section 18 and discharge section 24 lie in juxtaposition with the inlet section 22. These sections may be formed together in a manner similar to a double lumen catheter. The outlet end of the tubing 39 in the fluid source 12 is connected to the inlet end on the inlet section 22 of the irrigation tube 211 while the inlet tubing 15 on the vacuum source 11 is connected to the exit end 20 of the discharge section 21. Thus, it will be seen that the irrigation tube 211 passes into and out of the body part at the same opening so that neither end of the irrigation tube 211 need be pulled through the body part to remove the tube 11, thereby preventing contamination of the body part. It is preferable that the perforated section 18 be located on the exit side of the loop in the tube 211 so as to prevent any accumulation of foreign matter withdrawn from the body part during irrigation in the bend 212 of the tube 211. An irrigation tube conforming to tube 211 may be made using a larger tube 311 and seaming it down the middle as illustrated in FIG. 11 with a seam 312 and sealing it at one end as illustrated at 314. The seam 312 is stopped a prescribed distance $d_p$ from the sealed end 314 so that a common fluid passage that extends along one side of tube 311, around the end of seam 312 at the sealed end 314, and then back along the other side of tube 311. The tube 311 is separated at that end opposite the sealed end to form an inlet end 319 and outlet end 320 for respective connection to the fluid source 12 and vacuum source 14. Thus, one side of tube 311 serves as the inlet section 322 while the other side serves as the discharge section 321. The perforated section 318 is typically located in the discharge section 324 adjacent the sealed end 314 of tube 311 and has the discharge openings 321 formed therein as illustrated.

To facilitate the installation of the tube 311, it may be initially made by stopping the seam 312 a short distance $d_f$ from that end of tube 314 opposite the sealed end 314 as seen in FIG. 12 to form a single diameter pulling portion 315 defining a single passage therethrough so that the pulling portion 314 can be fastened to a trocar 58. The tube 311 is typically installed while that area of the body part to be irrigated is open during surgery. The trocar 58 can then be inserted from the opened inside of the body part out through the body part to pull the irrigation tube 311 into place so that the perforated section 318 therein is in registration with that portion of the body part to be irrigated. After the irrigation tube 311 in this condition has been pulled into place in the body part, the end of the irrigation tube 311 at the pulling portion 311 can be cut from the main portion of tube 311 along the cutting plane CP illustrated in FIG. 12 so as to open the two portions of the passage through the tube 311. The attached inlet end 19 and exit end 20 can then be separated as illustrated in FIG. 13 for attachment to the fluid source 12 and vacuum source 14. The seam 312 can also be sutured to the body part to help retain the tube 311 in place. In operation, the irrigation tube 311 would operate in the same manner as the previous embodiments described above.

There is also a problem encountered where the irrigation tube 11, 111₁–111₃, 211 or 311 passes out of the body part. This is because the tube can flex and thus shirt slightly with respect to the body part so as to irritate same. To overcome this problem, a mounting adapter 400 is illustrated in FIG. 11. The mounting adapter 100 includes a relatively large base 101 to which is attached an upstanding sleeve 102. The sleeve 402 and base 401 define a passage therethrough which will slidably receive the irrigation tube therethrough in a tight fit so that the irrigation tube is restrained from axial movement through the mounting adapter 400. Further means may be used to secure the mounting adapter 400 to the irrigation tube such as an adhesive. It will be appreciated that the height of the sleeve 402 is such that the point at which the irrigation tube is allowed to flex is shifted out to the projecting end of the sleeve 402. The base 401 may be made out of a soft cushiony material, or a soft cushiony layer 401 such as a foam rubber elastomer may be added to the bottom of base 101 so that the skin is exposed only to this soft cushiony material to prevent irritation.

The base 401 is sufficiently large to allow it to be attached to the outside surface of the body part over a large enough to prevent relative movement between the irrigation tube and the body part where it exits same. Any appropriate means such as tape, bandaging material, or an adhesive may be used to attach the base 401 to the body part. Thus, the problem of irritation of the body part where the irrigation tube enters or exits the body part can be overcome. In those instances where the irrigation tube enters the body part in one position and passes out of the body part in another position, two of the mounting adapters 400 would be used whereas only one adapter 400 would be needed for the irrigation tube 211 or 311. It will be appreciated that the diameter of the passage through the sleeve 402 would be appropriately varied to accommodate the different sizes and embodiments of the irrigation tube.

What is claimed as invention is:

1. A method of irrigating a wound in a body part with a treatment fluid comprising the steps of:
    placing a plurality of pieces of tubing in the body part, each of said pieces of tubing having a perforated section therein so that all of the perforated sections are located in the vicinity of the wound in the body part to be irrigated with the perforated section of each piece of tubing being shifted axially with respect to the perforated sections in the other pieces of tubing and with opposite ends of each piece of tubing projecting out of the body part;
    connecting one end of each of the pieces of tubing to a source of treatment fluid so that the pieces of tubing are connected to the source of treatment fluid in parallel with each other and so that the treatment fluid passes through the pieces of tubing into the body part and is discharged into the wound through the perforated sections; and
    connecting the opposite ends of the pieces of tubing to a vacuum source so that the pieces of tubing are connected to the vacuum source in parallel with each other and so that the vacuum is imposed through the pieces of tubing on the treatment fluid passing into the body part through the pieces of tubing and through the perforated sections on fluids in the body part surrounding the perforated sections in the pieces of tubing.

2. The method of claim 1 wherein the perforated section in each piece of tubing has a length no greater than three inches.

3. The method of claim 1 wherein the perforated section in each piece of tubing has a length no greater than two inches.

4. Apparatus for irrigating a portion of the body part with a treatment fluid comprising:
    a plurality of irrigation tubes, each having opposed ends and including a tubular side wall defining a fluid passage therethrough along the length thereof, each of said tubular side walls including a perforate section intermediate the ends of said tubing defining a plurality of perforate openings therethrough opening into said fluid passage so that fluid can flow through said perforate openings out of said fluid passage and into said fluid passage, said perforate section in each of said irrigation tubes axially shifted with respect to said perforate sections in the other of said irrigation tubes and said irrigation tubes adapted to be placed in the body part so that that portion of the body part to be irrigated is generally in registration with the perforate sections in said irrigation tubes;
    a fluid source to supply the treatment fluid at a controlled rate;
    first connector means connecting one end of each of said irrigation tubes to said fluid source in parallel with each other so that the treatment fluid flows in parallel through said fluid passages in said irrigation tubes;
    a vacuum source; and
    second connector means connecting the opposite ends of said irrigation tubes to said vacuum source in parallel with each other so that said vacuum source communicates with said fluid passages through the opposite ends of all of said irrigation tubes to impose a vacuum in parallel in said fluid passages so that, when said perforate sections are located in said body part, the treatment fluid from said fluid source flows along said fluid passages and out into the body part through said perforate openings, and fluid in the body part around said perforate sections will be withdrawn from the body part through said perforate openings and pass along said fluid passages in parallel and out of said opposite ends while at the same time, some of the treatment fluid from said fluid source will be forced along said fluid passages past said perforate sections and out of said opposite ends without flowing out of said fluid passages through said perforate openings while the vacuum is being imposed by said vacuum source.

5. The apparatus of claim 4 wherein said perforate section in each of said irrigation tubes has a length no greater than about three inches.

6. The apparatus of claim 4 further including mounting adapter means for selectively fixing said irrigation tube to the surface of the body part through which said irrigation tube passes.

7. Apparatus for irrigating a portion of a body part with a treatment fluid comprising:
    an irrigation tube having opposed ends and including an elongate tubular side wall defining a common fluid passage therethrough along the length thereof, said tubular side wall including a generally straight perforate section intermediate the ends of said tubing defining a plurality of perforate openings therethrough opening into said fluid passage so that fluid can flow through said perforate openings out of said fluid passage and into said fluid passage, said irrigation tube folded between said perforate section and a first of said opposed ends of said irrigation tube to form two portions in said irrigation tube lying in a side-by-side relationship joined by a bend, said irrigation tube adapted to be placed in the body part so that that portion of the body part to be irrigated is generally in registration with the perforate section with said opposed ends passing out of the body part through a common opening;

a fluid source communicating with said fluid passage through said first end of said irrigation tube continuously supplying the treatment fluid to said fluid passage at a controlled rate to flow along said fluid passage and around the bend therein to said perforate section; and a vacuum source communicating with said fluid passage through the opposite end of said irrigation tube to impose a vacuum in said fluid passage so that, when said perforate section is located in said body part, the treatment fluid from said fluid source flows along said fluid passage and out into the body part through said perforate openings, and fluid in the body part around said perforate section will be withdrawn from the body part through said perforate openings and pass along said fluid passage out of said opposite end while, at the same time, some of the treatment fluid from said fluid source will be forced along said fluid passage past said perforate section and out of said opposite end without flowing out of said fluid passage through said perforate openings while the vacuum is being imposed by said vacuum source.

8. Apparatus adapted to be connected to a fluid source and a vacuum source for irrigating a portion of a body part with a treatment fluid comprising:

an elongate irrigation tube including a tubular side wall defining a passage therethrough and having opposed ends, one of said ends being sealed to close said passage and the other of said ends being open, said side wall being longitudinally seamed together from a first position spaced a first prescribed distance from said sealed end to a second position spaced a second prescribed distance from said open end and defining a fluid passage extending from said open end of said tube along one side of the seam, around the end of the seam at said sealed end of said tube, and back along the other side of said seam to said open end of said tube, said tubular side wall defining a plurality of perforate openings therethrough opening into the fluid passage on one side of the seam so that fluid can flow out of and into the fluid passage through said perforate openings whereby said tube can be placed in the body part by engaging said open end and passing it through a single opening in the body part until that portion of the body part to be irrigated is generally in registration with said perforate openings and, after said tube is in place, those portions of the fluid passage on opposite sides of the seam can be separated by severing said tube adjacent said open end but across the seam whereby that portion of the fluid passage on that side of the seam into which said perforate openings open is connectable to the vacuum source while that portion of the fluid passage on the opposite side of the seam is connectable to the fluid source so that the treatment fluid from the fluid source flows along the fluid passage and out into the body part through said perforate openings, and fluid in the body part around said perforate openings will be withdrawn from the body part through said perforate openings and pass along the fluid passage out of its opposite end while at the same time, some of the treatment fluid from the fluid source will be forced along the fluid passage past said perforate openings without flowing out of said fluid passage through said perforate openings while the vacuum is being imposed by the vacuum source to keep the fluid passage clear.

9. Apparatus adapted to be connected to a fluid source and a vacuum source for irrigating a portion of a body part with a treatment fluid comprising:

a flexible irrigation tube having opposed ends and including a tubular side wall defining a fluid passage therethrough along the length thereof, said tubular side wall including a perforate section intermediate the ends of said tubing defining a plurality of perforate openings therethrough opening into said fluid passage so that fluid can flow through said perforate openings out of said fluid passage and into said fluid passage, said irrigation tube adapted to be placed in the body part so that opposite ends of the irrigation tube pass out of the body part and that portion of the body part to be irrigated is generally in registration with the perforate section; and a mounting adapter including a sleeve receiving said irrigation tube therethrough in a tight fit so that said irrigation tube is restrained from axial movement relative to said adapter and a base connected to one end of said sleeve and adapted to be connected to the body part about the point where said irrigation tube passes out of the body part to prevent relative movement between said irrigation tube and the body part at the point where said irrigation tube passes out of the body part.

* * * * *